US012527598B2

(12) United States Patent
Nelson et al.

(10) Patent No.: US 12,527,598 B2
(45) **Date of Patent: *Jan. 20, 2026**

(54) MEDICAL DEVICE FOR ACCESSING THE CENTRAL NERVOUS SYSTEM

(71) Applicant: PHARAOH NEURO, INC., Minneapolis, MN (US)

(72) Inventors: Brian Dale Nelson, Birchwood, MN (US); Don William Eldon Evans, Saint Paul, MN (US)

(73) Assignee: PHARAOH NEURO, INC., Minneapolis, MN (US)

( * ) Notice: Subject to any disclaimer, the term of this patent is extended or adjusted under 35 U.S.C. 154(b) by 26 days.

This patent is subject to a terminal disclaimer.

(21) Appl. No.: 18/629,018

(22) Filed: Apr. 8, 2024

(65) Prior Publication Data

US 2024/0252207 A1 Aug. 1, 2024

Related U.S. Application Data

(63) Continuation of application No. 17/155,972, filed on Jan. 22, 2021, now Pat. No. 11,974,775.

(60) Provisional application No. 62/964,394, filed on Jan. 22, 2020.

(51) Int. Cl.
*A61B 17/02* (2006.01)
*A61B 17/34* (2006.01)

(52) U.S. Cl.
CPC .. *A61B 17/3423* (2013.01); *A61B 2017/3443* (2013.01)

(58) Field of Classification Search
None
See application file for complete search history.

(56) References Cited

U.S. PATENT DOCUMENTS

| | | | |
|---|---|---|---|
| 3,804,750 | A | 4/1974 | Myers et al. |
| 4,130,113 | A | 12/1978 | Graham |
| 5,779,681 | A | 7/1998 | Bonn |
| 6,730,021 | B2 | 5/2004 | Vassiliades et al. |
| 6,923,799 | B1 | 8/2005 | Asfora |

(Continued)

FOREIGN PATENT DOCUMENTS

| | | | |
|---|---|---|---|
| CN | 201824152 | U | 5/2011 |
| EP | 1970012 | A1 | 9/2008 |

(Continued)

OTHER PUBLICATIONS

Kuan et al. "Conceptual Design of a New Neurosurgical Brain Retractor" Mechanisms, Transmissions and Applications, vol. 31: pp. 261-269 Feb. 2015.

(Continued)

*Primary Examiner* — Jan Christopher L Merene
(74) *Attorney, Agent, or Firm* — Seager, Tufte & Wickhem LLP

(57) ABSTRACT

Medical devices for accessing the central nervous system, as well as making and using medical devices, are disclosed. An example medical device may include an expandable access port. The expandable access port may include a housing having a plurality of tines coupled thereto. A thrust washer may be disposed along the housing. An actuation member may be coupled to the housing. The actuation member may be designed to shift the plurality of tines between a first configuration and an expanded configuration.

20 Claims, 15 Drawing Sheets

(56) References Cited

U.S. PATENT DOCUMENTS 7,150,714 B2 12/2006 Myles
7,182,729 B2 2/2007 Abdelgany et al.
7,195,592 B2 * 3/2007 Ravikumar ............ A61B 17/02 600/219
7,204,840 B2 4/2007 Skakoon et al.
7,235,084 B2 6/2007 Skakoon et al.
7,374,534 B2 5/2008 Dalton
7,393,322 B2 7/2008 Wenchell
7,435,219 B2 10/2008 Kim
7,473,223 B2 1/2009 Fetzer
7,481,766 B2 1/2009 Lee et al.
7,513,869 B2 4/2009 Branch et al.
7,553,290 B1 6/2009 Asfora
7,594,888 B2 9/2009 Raymond et al.
7,645,232 B2 1/2010 Shluzas
7,691,120 B2 4/2010 Shluzas et al.
7,694,821 B1 4/2010 Asfora
7,758,501 B2 7/2010 Frasier et al.
7,766,823 B2 8/2010 Moll et al.
7,815,651 B2 10/2010 Skakoon et al.
7,828,809 B2 11/2010 Skakoon et al.
7,833,231 B2 11/2010 Skakoon et al.
7,850,608 B2 12/2010 Hamada
7,857,820 B2 12/2010 Skakoon et al.
7,892,174 B2 2/2011 Hestad et al.
7,896,088 B2 3/2011 Guerrero et al.
7,931,589 B2 4/2011 Cohen et al.
7,935,053 B2 5/2011 Karpowicz et al.
7,981,031 B2 7/2011 Frasier et al.
8,029,493 B2 10/2011 Asfora
8,105,236 B2 1/2012 Malandain et al.
8,123,682 B2 2/2012 Wenchell
8,152,721 B2 4/2012 Michaeli et al.
8,291,781 B2 10/2012 Guerrero et al.
8,328,844 B2 12/2012 Wenchell
8,343,138 B2 1/2013 Asfora
8,353,826 B2 1/2013 Weiman
8,360,970 B2 1/2013 Mangiardi
8,409,083 B2 4/2013 Mangiardi
8,409,089 B2 4/2013 Michaeli et al.
8,454,504 B2 6/2013 Michaeli et al.
8,517,935 B2 8/2013 Marchek et al.
8,550,995 B2 10/2013 Frasier et al.
8,574,154 B2 11/2013 Loftus et al.
8,579,809 B2 11/2013 Parker
8,602,984 B2 12/2013 Raymond et al.
8,608,650 B2 12/2013 Mangiardi
8,622,897 B2 1/2014 Raymond et al.
8,663,102 B2 3/2014 Michaeli et al.
8,733,453 B2 5/2014 Guerrero et al.
8,845,656 B2 9/2014 Skakoon et al.
8,876,687 B2 11/2014 Jones et al.
8,894,573 B2 11/2014 Loftus et al.
8,894,574 B2 11/2014 Ellman
8,911,452 B2 12/2014 Skakoon et al.
8,956,285 B2 2/2015 Gephart et al.
8,961,535 B2 2/2015 Burg et al.
8,974,380 B2 3/2015 Michaeli et al.
8,992,425 B2 3/2015 Karpowicz et al.
8,992,558 B2 3/2015 Stone et al.
9,028,402 B2 5/2015 Wenchell
9,161,820 B2 10/2015 Mark et al.
9,169,634 B2 10/2015 Guerrero et al.
9,179,903 B2 11/2015 Cianfrani et al.
9,186,175 B2 11/2015 Mark et al.
9,216,015 B2 12/2015 Wilson
9,265,523 B2 2/2016 Mark et al.
9,307,969 B2 4/2016 Novak et al.
9,386,974 B2 7/2016 Wilson
9,387,010 B2 7/2016 Mark et al.
9,492,065 B2 11/2016 Tesar et al.
9,566,052 B2 2/2017 Novak
9,579,121 B2 2/2017 Mark et al.
9,622,777 B2 4/2017 Mark et al.
9,675,331 B2 6/2017 Mangiardi
9,693,761 B2 7/2017 Fedorov et al.
9,737,287 B2 8/2017 Gifford et al.
9,757,147 B2 9/2017 Mark et al.
9,770,261 B2 9/2017 Mark et al.
9,782,157 B2 10/2017 Novak et al.
9,855,027 B2 1/2018 Ziolo et al.
9,949,814 B2 4/2018 Alexander et al.
9,968,414 B2 5/2018 Wilson
9,968,415 B2 5/2018 Wilson
9,980,745 B2 5/2018 Burg et al.
10,022,520 B2 7/2018 Mark
10,105,485 B2 10/2018 Piferi et al.
10,143,366 B2 12/2018 Mark et al.
11,707,294 B2 * 7/2023 Brown ............ A61M 25/09041 600/184
2006/0206008 A1 9/2006 Dalton
2006/0271096 A1 11/2006 Hamada
2006/0287583 A1 12/2006 Mangiardi
2007/0060939 A1 3/2007 Lancial et al.
2011/0054405 A1 3/2011 Whiting et al.
2011/0301421 A1 12/2011 Michaeli et al.
2013/0190575 A1 7/2013 Mast et al.
2013/0261402 A1 10/2013 Hawkins et al.
2014/0114138 A1 4/2014 Fedorov et al.
2014/0275801 A1 9/2014 Menchaca et al.
2015/0223832 A1 8/2015 Swaney et al.
2015/0366583 A1 * 12/2015 Druma ............... A61B 17/0218 600/204
2016/0128720 A1 5/2016 Mark et al.
2016/0128722 A1 5/2016 Mark et al.
2016/0278755 A1 9/2016 Stone et al.
2016/0317182 A1 11/2016 Mark et al.
2016/0317795 A1 11/2016 Mark et al.
2017/0000579 A1 1/2017 Mark et al.
2017/0215860 A1 8/2017 Trimarche et al.
2017/0265879 A1 9/2017 Washburn, II et al.
2017/0265893 A1 9/2017 Mark et al.
2017/0265894 A1 9/2017 Mark et al.
2017/0333017 A1 11/2017 Gifford et al.
2017/0367731 A1 12/2017 Mark et al.
2018/0125471 A1 5/2018 Schaefer
2018/0125603 A1 5/2018 Cantor et al.
2018/0263660 A1 9/2018 Burg et al.
2018/0296797 A1 10/2018 Mark
2019/0247087 A1 8/2019 Brown et al.
2024/0008896 A1 * 1/2024 Cantor ............... A61B 17/0293

FOREIGN PATENT DOCUMENTS

JP 2013523413 A 6/2013
WO 2007075791 A2 7/2007
WO 2011130532 A2 10/2011
WO 2019046940 A1 3/2019
WO 2019161305 A1 8/2019

OTHER PUBLICATIONS

International Search Report and Written Opinion dated May 14, 2019 for International Application No. PCT/US2019/018354.
International Search Report and Written Opinion dated Apr. 15, 2021 for International Application No. PCT/US2021/014972.

* cited by examiner

MEDICAL DEVICE FOR ACCESSING THE CENTRAL NERVOUS SYSTEM

CROSS REFERENCE TO RELATED APPLICATIONS

The present application is a continuation of U.S. patent application Ser. No. 17/155,972, Filed Jan. 22, 2021, which claims the benefit of and priority to U.S. Provisional Patent Application Ser. No. 62/964,394, filed on Jan. 22, 2020, entitled MEDICAL DEVICE FOR ACCESSING THE CENTRAL NERVOUS SYSTEM, the disclosures of which are incorporated herein by reference.

TECHNICAL FIELD

The present disclosure pertains to medical devices, and methods for manufacturing medical devices. More particularly, the present disclosure pertains to medical devices for accessing the central nervous system.

BACKGROUND

A wide variety of medical devices have been developed for medical use. Some of these devices include access sheaths, guidewires, catheters, and the like. These devices are manufactured by any one of a variety of different manufacturing methods and may be used according to any one of a variety of methods. Of the known medical devices and methods, each has certain advantages and disadvantages. There is an ongoing need to provide alternative medical devices as well as alternative methods for manufacturing and using medical devices.

BRIEF SUMMARY

This disclosure provides design, material, manufacturing method, and use alternatives for medical devices. An expandable access port is disclosed. The expandable access port comprises: a housing having a plurality of tines coupled thereto; a thrust washer disposed along the housing; and an actuation member coupled to the housing, the actuation member being designed to shift the plurality of tines between a first configuration and an expanded configuration.

Alternatively or additionally to any of the embodiments above, the plurality of tines include a first tine having a proximal end region with an angled surface.

Alternatively or additionally to any of the embodiments above, the thrust washer includes a cutout region configured to engage the proximal end region.

Alternatively or additionally to any of the embodiments above, the actuation member includes an actuation surface designed to engage the angled surface.

Alternatively or additionally to any of the embodiments above, the thrust washer is disposed between the housing and the actuation member.

Alternatively or additionally to any of the embodiments above, the housing includes a threaded region.

Alternatively or additionally to any of the embodiments above, the actuation member includes a nut threadably engaged with the threaded region.

Alternatively or additionally to any of the embodiments above, further comprising a sleeve extending along at least some of the plurality of tines.

Alternatively or additionally to any of the embodiments above, the sleeve includes a biocompatible elastomer.

Alternatively or additionally to any of the embodiments above, the sleeve is capable of elongating up to 400-1200%.

Alternatively or additionally to any of the embodiments above, the sleeve is capable of elongating up to 600-1000%.

Alternatively or additionally to any of the embodiments above, the sleeve is capable of elongating up to 800%.

An expandable access port is disclosed. The expandable access port comprises: a housing having a plurality of tines coupled thereto; a sleeve extending along at least some of the plurality of tines; wherein the sleeve includes a biocompatible elastomer; and an actuation member coupled to the housing, the actuation member being designed to shift the plurality of tines between a first configuration and an expanded configuration.

Alternatively or additionally to any of the embodiments above, the sleeve is capable of elongating up to 400-1200%.

Alternatively or additionally to any of the embodiments above, the sleeve is capable of elongating up to 600-1000%.

Alternatively or additionally to any of the embodiments above, the sleeve is capable of elongating up to 800%.

Alternatively or additionally to any of the embodiments above, further comprising a thrust washer disposed along the housing.

Alternatively or additionally to any of the embodiments above, the thrust washer is disposed between the housing and the actuation member.

Alternatively or additionally to any of the embodiments above, the plurality of tines include a first tine having a proximal end region with an angled surface.

Alternatively or additionally to any of the embodiments above, the thrust washer includes a cutout region configured to engage the proximal end region.

Alternatively or additionally to any of the embodiments above, the actuation member includes an actuation surface designed to engage the angled surface.

Alternatively or additionally to any of the embodiments above, the housing includes a threaded region.

Alternatively or additionally to any of the embodiments above, the actuation member includes a nut threadably engaged with the threaded region.

An expandable access port is disclosed. The expandable access port comprises: a housing having a plurality of tines coupled thereto and having a threaded region; an actuation nut coupled to the threaded region, the actuation nut being designed to shift the plurality of tines between a first configuration and an expanded configuration; a thrust washer disposed between the housing and the actuation nut; and a sleeve extending along at least some of the plurality of tines, the sleeve including a biocompatible elastomer.

Alternatively or additionally to any of the embodiments above, the sleeve is capable of elongating up to 400-1200%.

Alternatively or additionally to any of the embodiments above, the sleeve is capable of elongating up to 600-1000%.

Alternatively or additionally to any of the embodiments above, the sleeve is capable of elongating up to 800%.

Alternatively or additionally to any of the embodiments above, the plurality of tines include a first tine having a proximal end region with an angled surface.

Alternatively or additionally to any of the embodiments above, the thrust washer includes a cutout region configured to engage the proximal end region.

Alternatively or additionally to any of the embodiments above, the actuation nut includes an actuation surface designed to engage the angled surface.

A system is disclosed. The system comprises an expandable access port including a housing having a plurality of tines coupled thereto, a thrust washer disposed along the housing, an actuation member coupled to the housing, the actuation member being designed to shift the plurality of tines between a first configuration and an expanded configuration. The system also includes an obturator including a shaft and nose cone, and a guide having a lumen configured to receive the obturator, the guide configured to mate with the housing.

The above summary of some embodiments is not intended to describe each disclosed embodiment or every implementation of the present disclosure. The Figures, and Detailed Description, which follow, more particularly exemplify these embodiments.

BRIEF DESCRIPTION OF THE DRAWINGS

The disclosure may be more completely understood in consideration of the following detailed description in connection with the accompanying drawings, in which.

Figure 1:
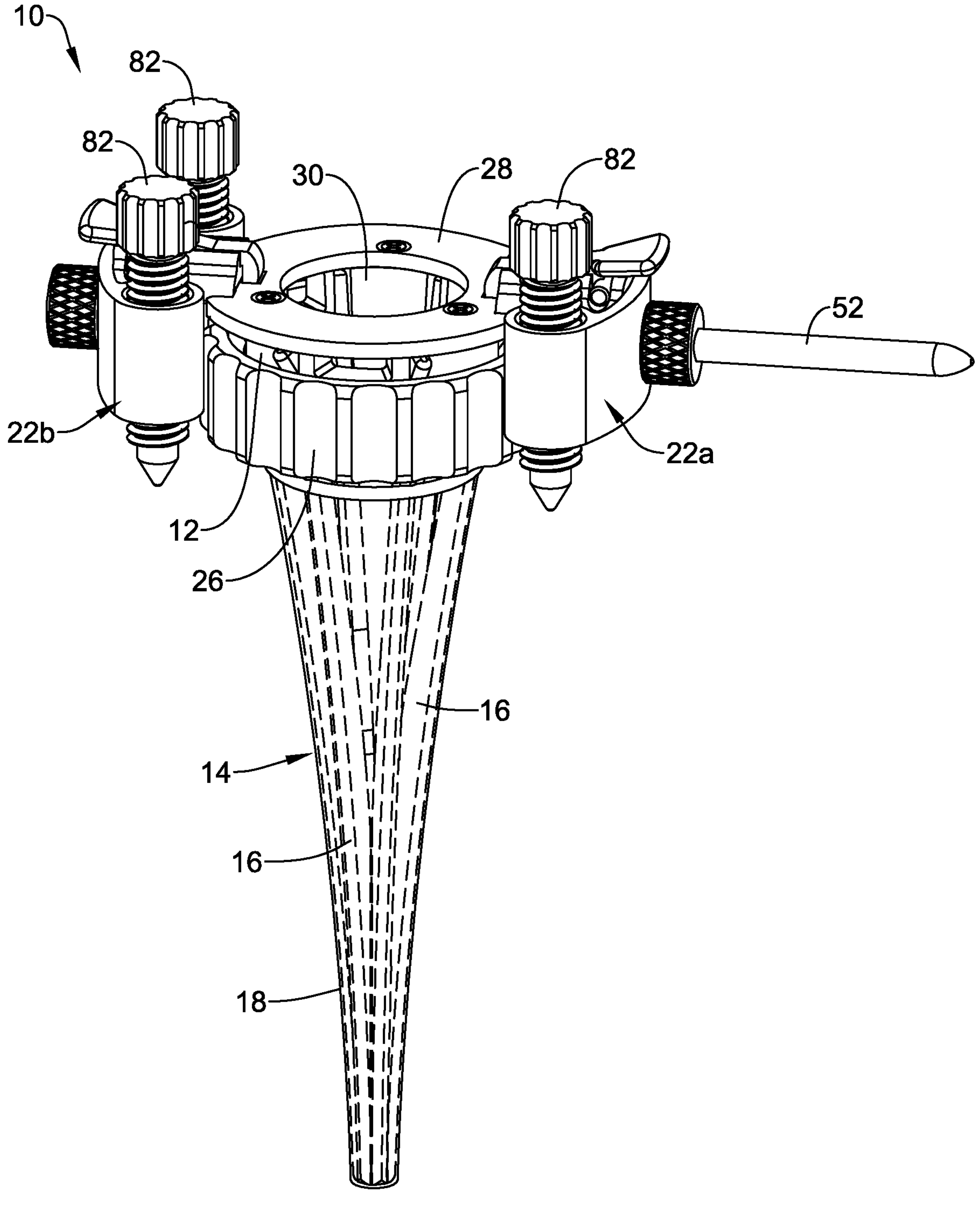
FIG. 1 is a perspective view of an example expandable access port.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about", whether or not explicitly indicated. The term "about" generally refers to a range of numbers that one of skill in the art would consider equivalent to the recited value (e.g., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar elements in different drawings are numbered the same. The drawings, which are not necessarily to scale, depict illustrative embodiments and are not intended to limit the scope of the invention.

Lesions, clots, tumors, and/or other malformations in the brain may be challenging to treat. At least some of the challenges associated with such treatments may be associated with gaining access to the target side. For example, accessing a clot within the brain may require navigating a treatment device through regions of the brain. This may require relatively delicate traversal through brain tissue. It may be desirable to access regions of the brain in a manner that reduces trauma to the brain tissue, increases the ability to image/visualize regions of the brain, and/or otherwise provides better access to a target region. Disclosed herein are medical devices that are designed to provide improved access to body regions including regions along the central nervous system and/or the brain. Also disclosed are methods for making and using such devices.

FIG. 1 is a perspective view of a portion of an example expandable access port or sheath 10 for accessing the central nervous system. The expandable access port 10 may include a housing 12 and an expandable conduit 14 coupled to the housing 12. In general, the expandable conduit 14 may be designed to be inserted into a body opening, cavity, or the like in order to provide access to a target region. For example, the expandable conduit 14 may be designed to be inserted through an opening in the head of a patient, through the skull, and into the brain so as to provide access to a target (e.g., a lesion, clot, tumor, or the like, etc.) within the brain. Furthermore, due to the expandable conduit 14 being "expandable", the expandable conduit 14 can be placed near a target site (e.g., within the brain) and expanded. When doing so, the expandable conduit 14 may atraumatically push, move, and/or otherwise expand brain tissue adjacent to the target site, which may provide for better access, visualization (e.g. including direct visualization by a clinician through the expandable conduit 14), etc. of the target site.

The expandable access port 10 may include a number of structural features. For example, the expandable conduit 14 may include a plurality of tines 16. A sleeve 18 may be disposed along the tines 16. In some instances, the sleeve 18 may include an elastomeric material and/or a biocompatible elastomer. The elastomeric material and/or a biocompatible elastomer may have a hardness in the range of about 3 Shore A to about 10 Shore A. In at least some instances, the elastomeric material and/or a biocompatible elastomer is at least partially light transmissive. For example, the elastomeric material and/or a biocompatible elastomer may be substantially transparent. In at least some instances, the sleeve 18 may include a thermoplastic rubber elastomer such as CHRONOPRENE (e.g., such as CHRONOPRENE 5A, commercially available from AdvanSource Biomaterials, Wilmington, MA). In some instances, the sleeve 18 may be capable of elongating up to about 400-1200%, or up to about 600-1000%, or up to about 800%. Furthermore, in some instances the sleeve 18 may be substantially resistant to tearing or hole propagation. Thus, if the sleeve 18 is elongated up to about 800%, a relatively small hole poked through the sleeve 18 will resist tearing at the hole and/or propagation/propagating at the hole. In other words, when the sleeve 18 is elongated (e.g., highly elongated), a puncture in the sleeve 18 will resist propagating (e.g., the puncture will not propagate). In some instances the sleeve 18 is substantially puncture resistant at up to about 800% elongation at the hole.

Figure 2:
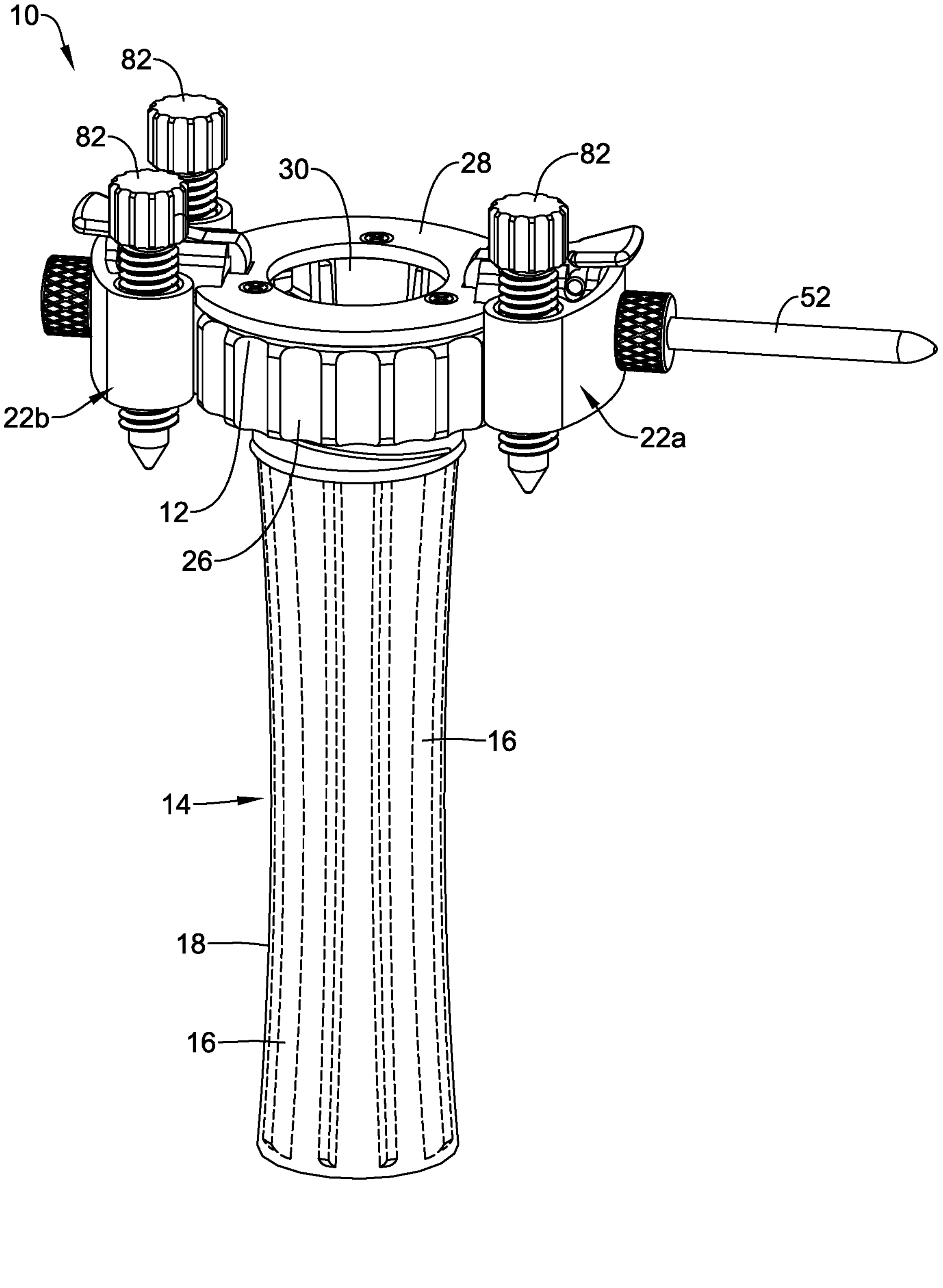
FIG. 2 is a perspective view of an example expandable access port.

The housing 12 may include a cap 28 and a distal opening 30. An actuation member 26 may be coupled to the housing 12. The actuation member 26 may be used to shift the expandable conduit 14 between a first configuration (e.g., as shown in FIG. 1) and a second or expanded configuration (e.g., as shown in FIG. 2). In this example, the actuation member 26 takes the form of a nut. The nut 26 can be rotated about threads along the housing 12. When doing so, the nut 26 engages the tines 16 in order to shift the tines 16 (e.g., and/or the expandable conduit 14) between the first and second configurations. In at least some instances, frictional forces between the housing 12 (e.g., the threaded region 64 along the housing 12 as depicted in FIG. 3) and the nut 26 (e.g., the threads 86 along the nut/actuation member 26 as depicted in FIG. 3A) may help hold, secure, and/or otherwise lock the tines 16 (e.g., and/or the expandable conduit 14) in, for example, the second configuration.

One or more adjustment mechanisms, for example a first adjustment mechanism 22*a* and a second adjustment mechanism 22*b*, may be coupled to the cap 28. The form of the first adjustment mechanism 22*a*, the second adjustment mechanism 22*b*, or both may vary. For example, in some instances the first adjustment mechanism 22*a* may include a threaded leg 82 that may be used to adjust the position of the expandable access port 10 relative to the patient. The first adjustment mechanism 22*a* may also include a stabilizing bar 52, which may be used to couple/secure the expandable access port 10 to a stabilizing system (not shown). Some example stabilizing systems that may be used with the stabilizing bar 52 may include those manufactured by INTEGRA, MIZUHO, TEDAN SURGICAL, as well as systems including GREENBERG, BUDDE, SUGITA, FUKUSHIMA, and the like. The second adjustment mechanism 22*b* may include one or more threaded legs 82 that may be used to adjust the position of the expandable access port 10 relative to the patient. Other adjustment mechanisms are contemplated that include a single threaded leg 82, two or more threaded legs 82, lack a threaded leg 82, a single stabilizing bar 52, two more stabilizing bars 52, lack a stabilizing bar 52, and the like.

Figure 3:
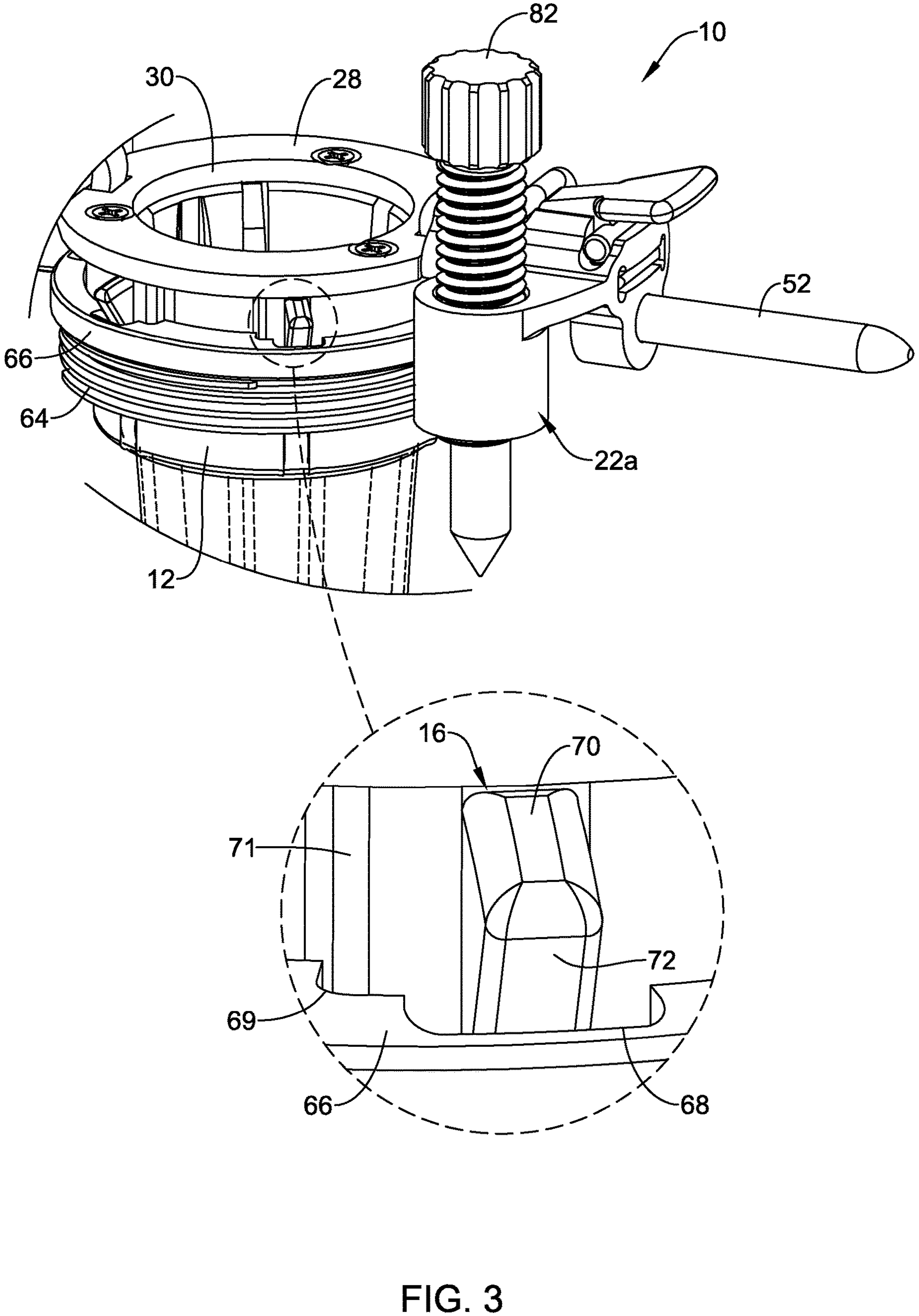
FIG. 3 is a perspective view of an example expandable access port.
Figure 3A:
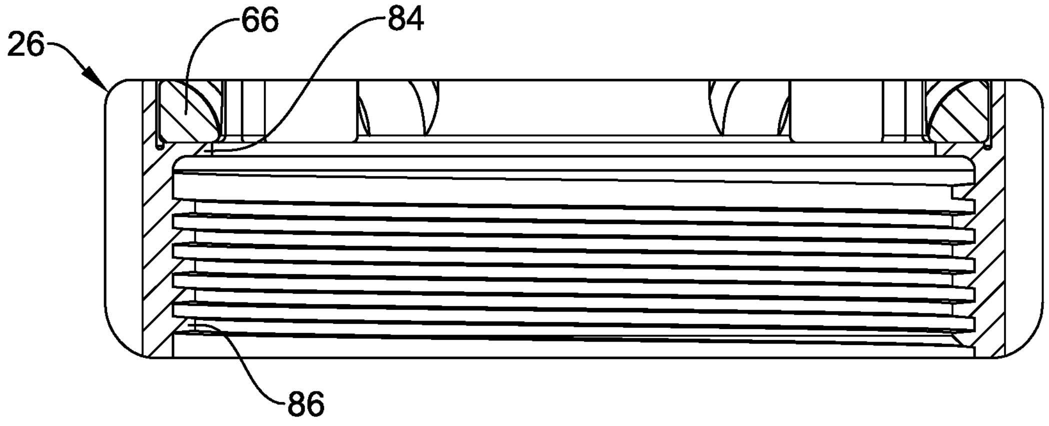
FIG. 3A is a partial cross-sectional view of a portion of an expandable access port.

FIG. 3 illustrates a portion of the expandable access port 10. In this view, the actuation member 26 is removed so that the threaded region 64 of the housing 12 can be seen. In addition, FIG. 3 also illustrates that a thrust washer 66 may be disposed along the housing 12. The thrust washer 66 is generally disposed between the actuation member 26 and the housing 12 and is designed to help reduce sliding forces so that the actuation member 26 can be rotated easily. In some instances, the thrust washer 66 may be disposed adjacent to a flange or actuation surface 84 of the actuation member 26 as shown in FIG. 3A. The actuation surface 84 may positioned adjacent to an internal thread or threaded region 86 of the actuation member 26. The thrust washer 66 may include a cutout region 68. A proximal end region 70 of the tines 16 (e.g., having an angled surface 72) may be disposed within and/or otherwise engaged with the cutout region 68. A portion 69 of the cutout region 68 may also help to secure the thrust washer 66 in place by engaging a section 71 of the housing 12 between adjacent tines 16. Actuation of the actuation member 26 (e.g., by rotation thereof) may cause the actuation member 26 (e.g., the actuation surface 86) to engage the tines 16 (e.g., the proximal end region 70 and/or the angled surface 72 of the tines 16) so as to shift the tines 16 (e.g., and the expandable conduit 14) between the first and second configurations.

Figure 4:
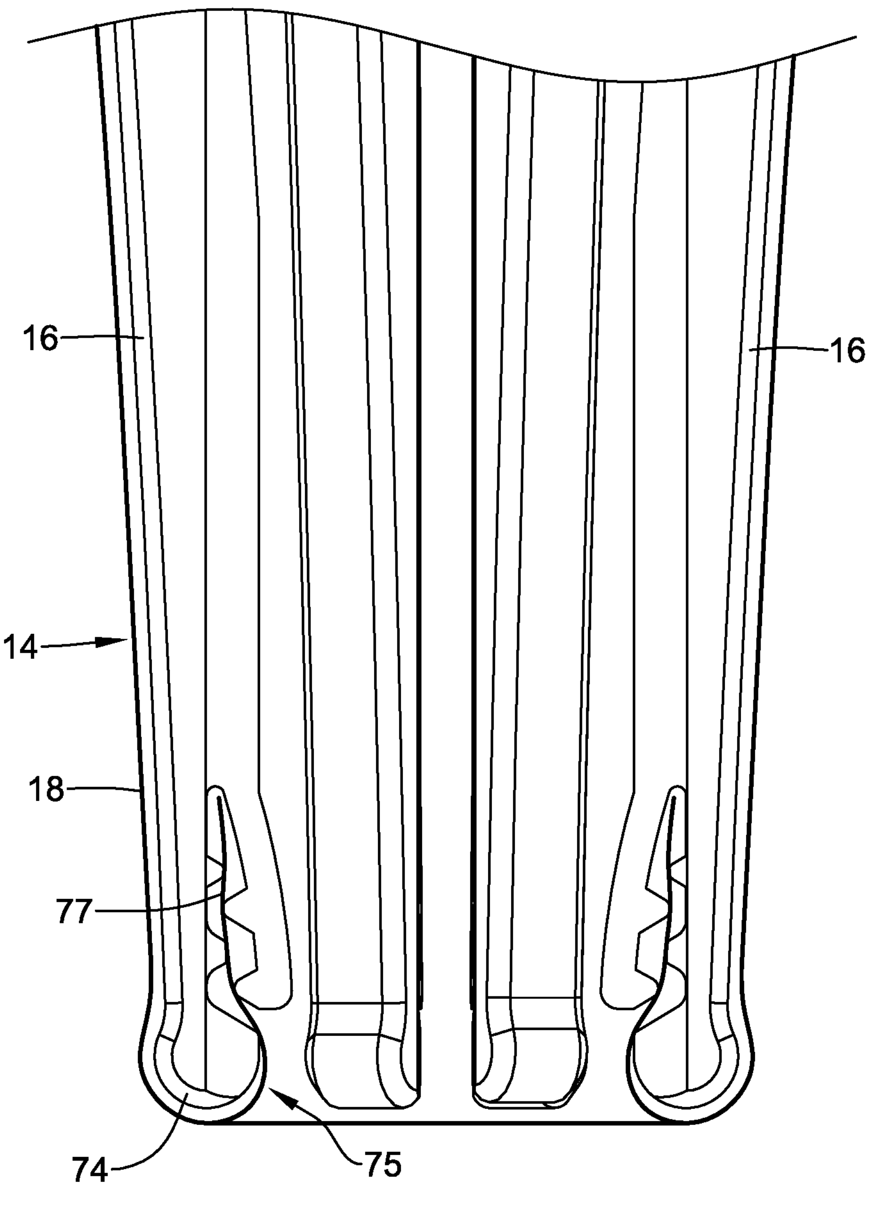
FIG. 4 illustrates a portion of an example expandable access port.

FIG. 4 illustrates a portion of the expandable access port 10. Here it can be seen that at the distal ends 74 of the tines 16 may include a crimp region 75. An end portion 77 of the sleeve 18 may engage the crimp region 75. For example, the end portion 77 may be inserted into the crimp region 75 and the crimp region 75 may be crimped. This may help to secure the sleeve 18 to the tines 16.

Figure 5:
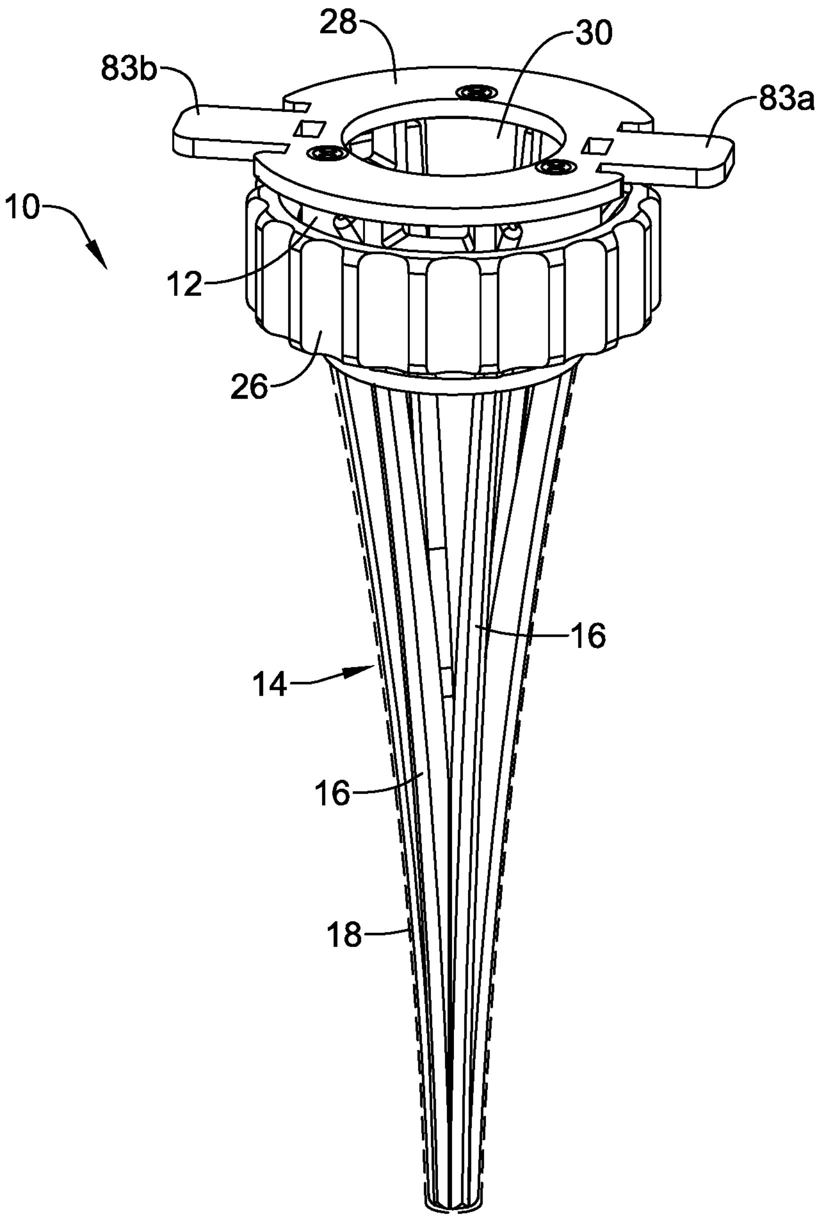
FIG. 5 is a perspective view of an example expandable access port.
Figure 6:
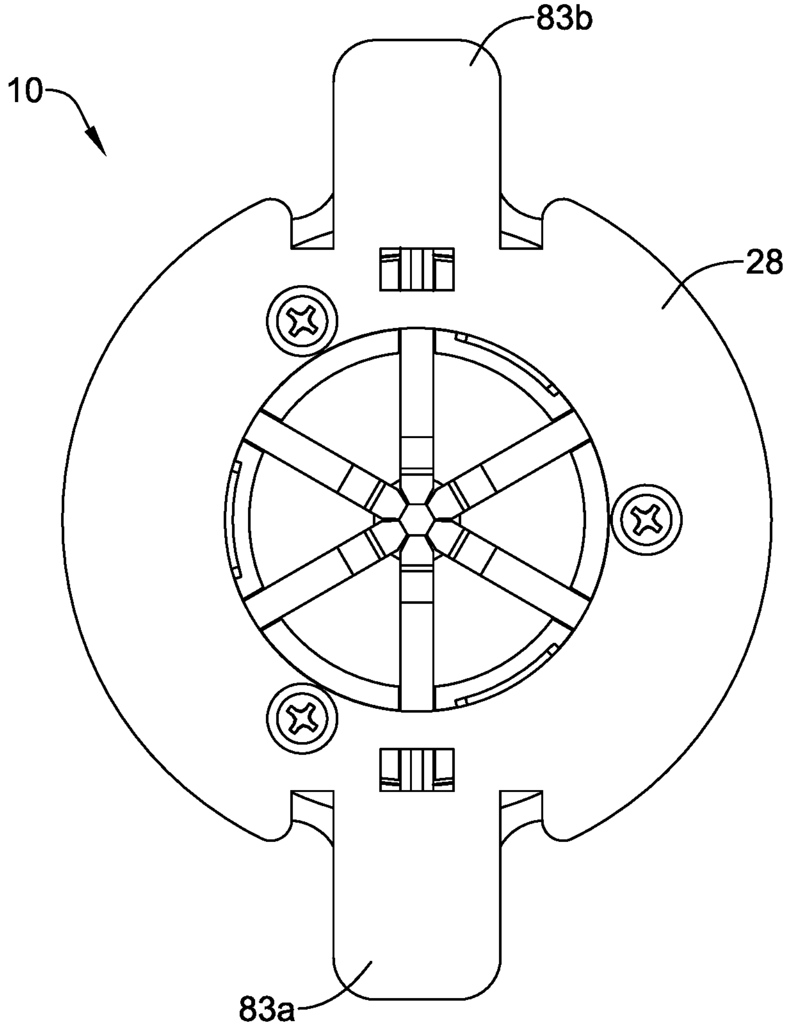
FIG. 6 is a top view of an example expandable access port.
Figure 7:
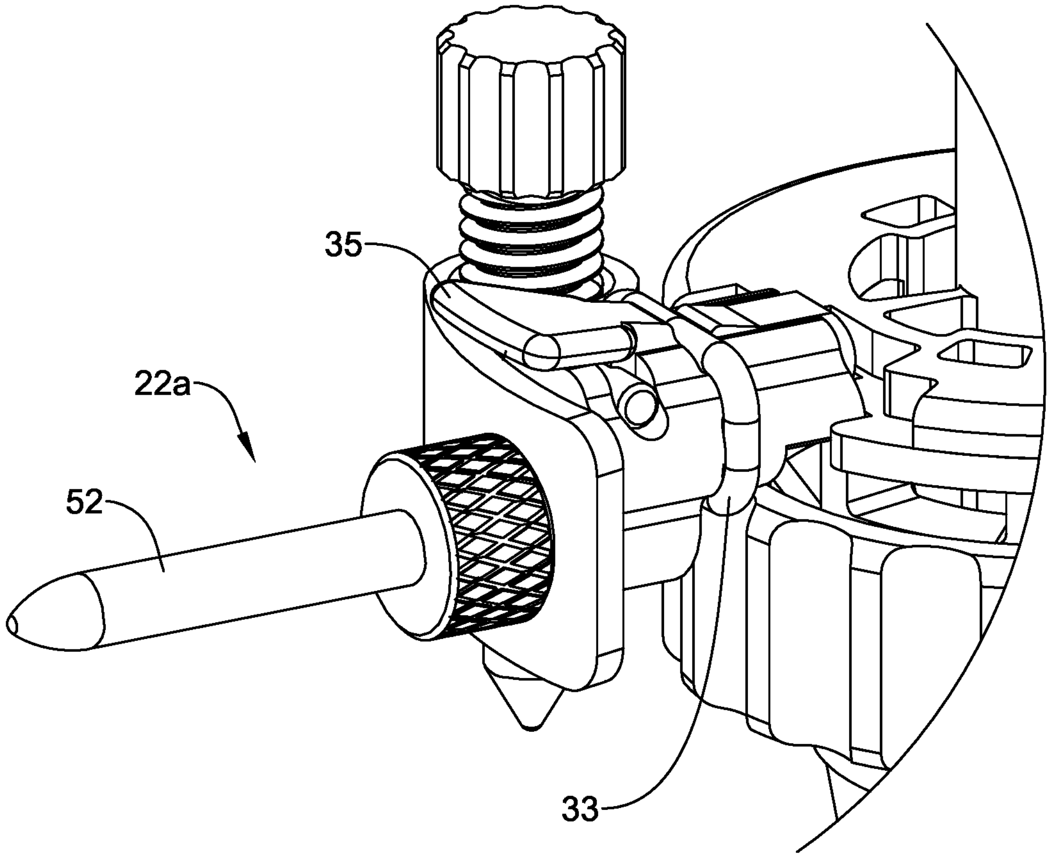
FIG. 7 is a perspective view of an example expandable access port.

FIGS. 5-6 illustrates the expandable access port 10 with the first adjustment mechanism 22*a* and the second adjustment mechanism 22*b* detached from the cap 28. Here it can be seen that the cap 28 may include a first attachment region 83*a* and a second attachment region 83*b*. In at least some instances, the first attachment region 83*a* and the second attachment region 83*b* allow for a variety of adjustment mechanisms to be releasably coupled thereto. For example, the first attachment region 83*a* and/or the second attachment region 83*b* may take the form of a flange designed to have an adjustment mechanism (e.g., the first adjustment mechanism 22*a*, the second adjustment mechanism 22*b*, or both) releasably attached to the cap 28. The adjustment mechanisms 22*a*/22*b* may include spring-release attachment/detachment mechanism including a spring or clastic member 33 and a lever member 35 as shown in FIG. 7. In some instances, the elastic member 33 takes the form of an O-ring that is used as or like a spring to hold down the lever member 35 (e.g., so that adjustment mechanisms 22*a*/22*b* can be securely attached to the attachment regions 83*a*/83*b*). The lever member 35 can be depressed to enlarge or otherwise expand the elastic member 33. This allows the adjustment mechanisms 22*a*/22*b* to easily be securely attached/detached from the attachment regions 83*a*/83*b*, as desired.

Figure 8:
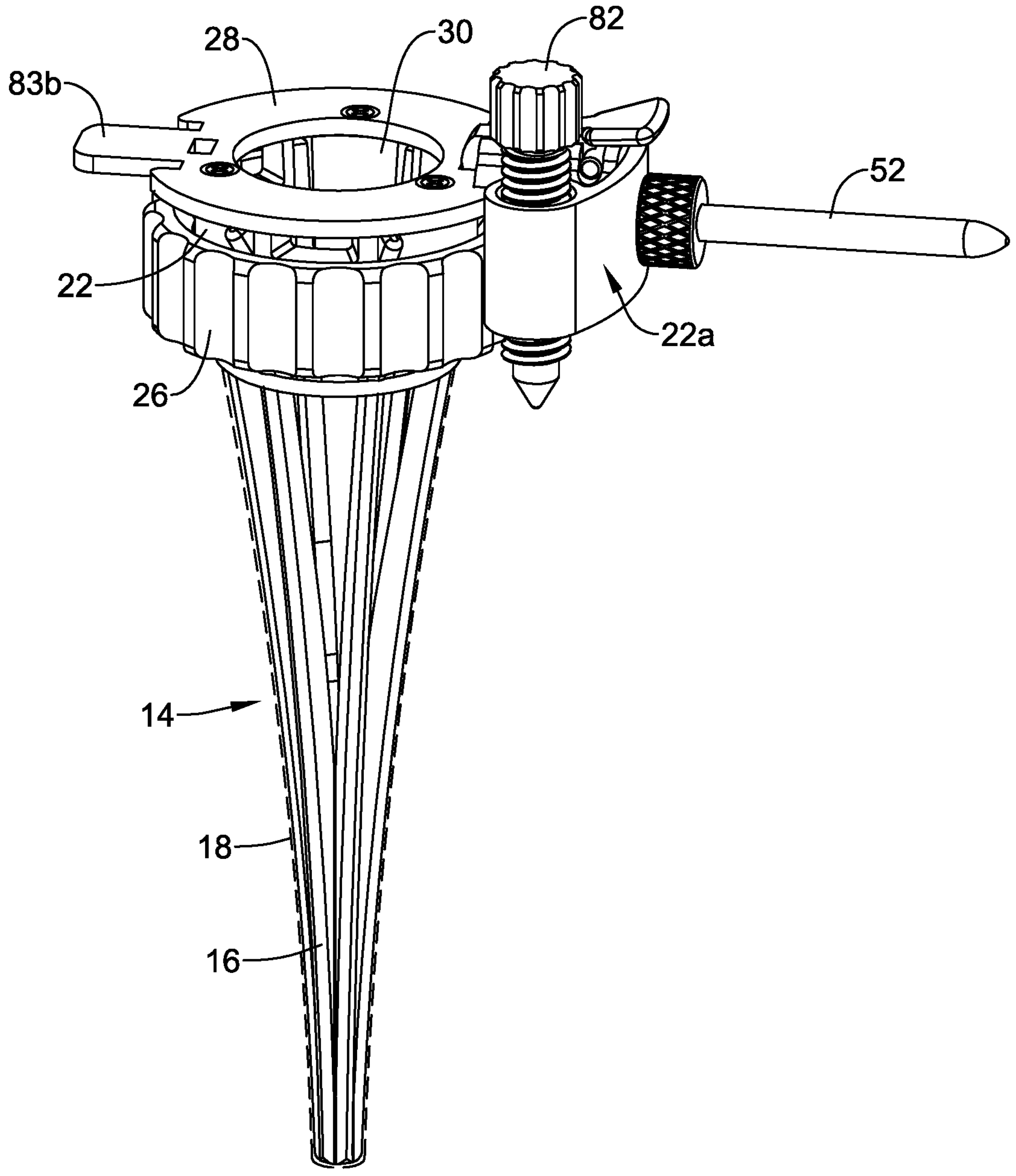
FIG. 8 is a perspective view of a portion of an example expandable access port.
Figure 9:
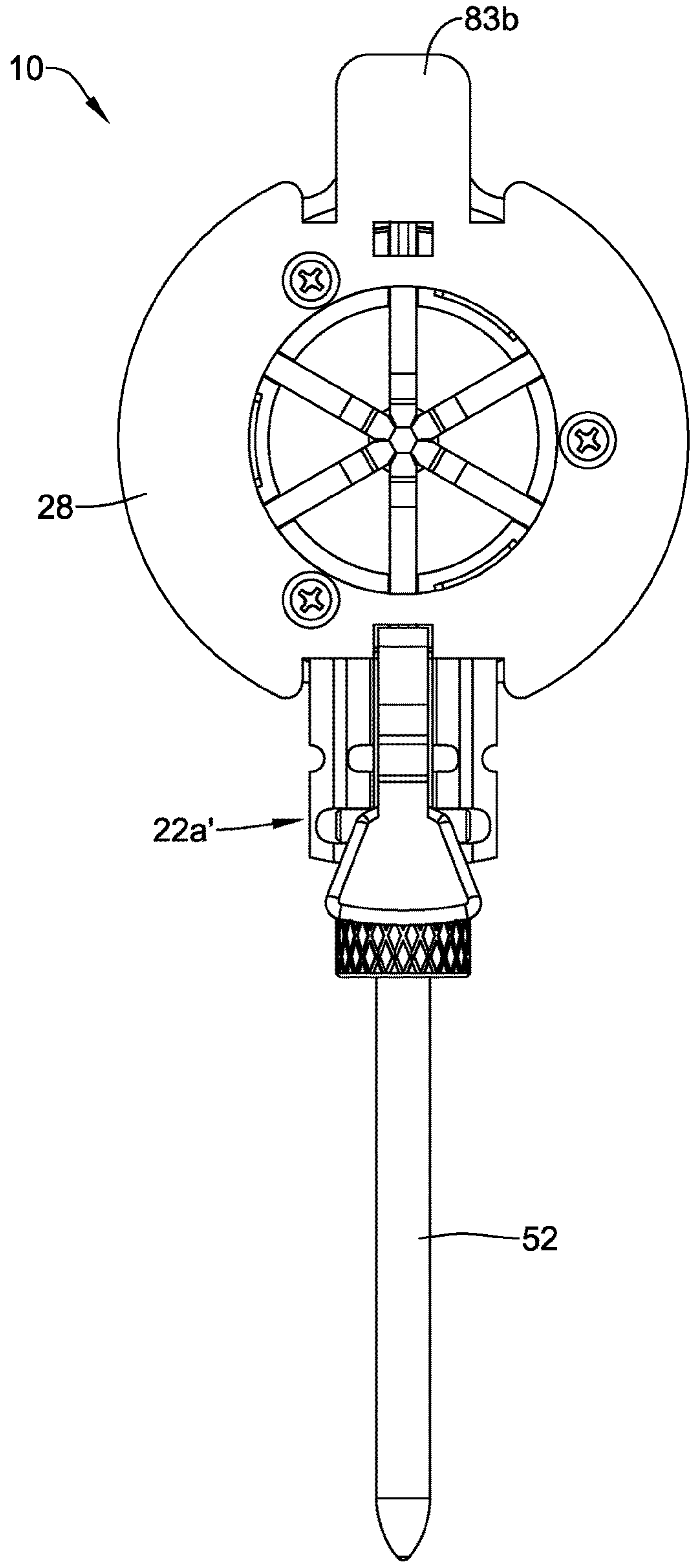
FIG. 9 is a top view of an example expandable access port.

In use, a clinician may choose to attach a suitable number of adjustment mechanisms to the cap 28 (e.g., the first attachment region 83*a* and/or the second attachment region 83*b*). The form or type of adjustment mechanism may vary and, in at least some instances, the type of adjustment mechanism may be selected in order to best suit the needs of a particular intervention. For example, the first adjustment mechanism 22*a* may be attached to the first attachment region 83*a* as shown in FIG. 8. In this example, an adjustment mechanism is not attached to the second attachment region 83*b*. Further illustrating the variability of the adjustment mechanisms contemplated, FIG. 9 illustrates another adjustment mechanism 22*a*' attached to the cap 28 (e.g., the first attachment region 83*a*) of the expandable access port 10. In this example, the adjustment mechanism 22*a*' includes the stabilizing bar 52 but does not include a set screw. Other variations are contemplated.

Figure 10:
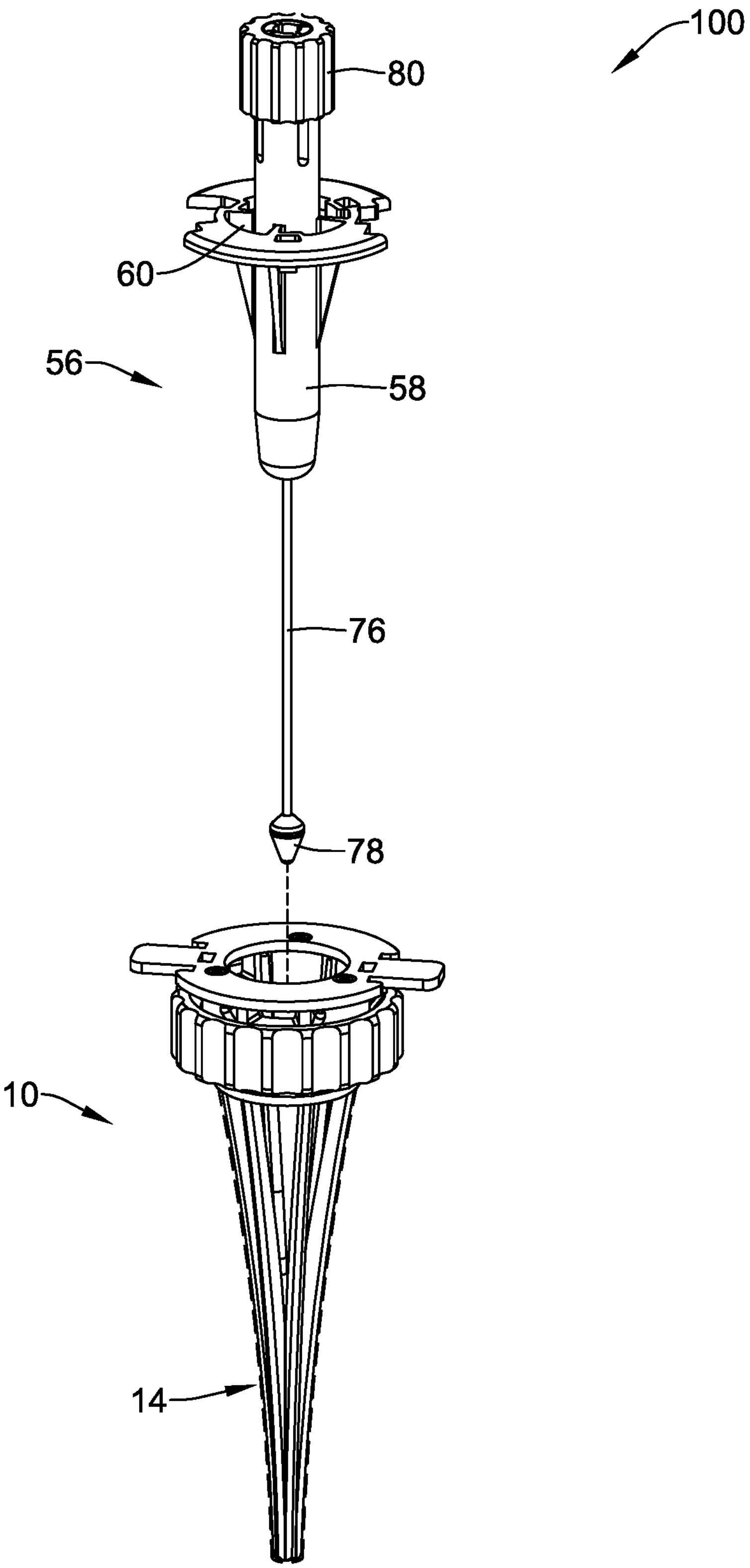
FIG. 10 is a plan view of a system for accessing the central nervous system.
Figure 11:
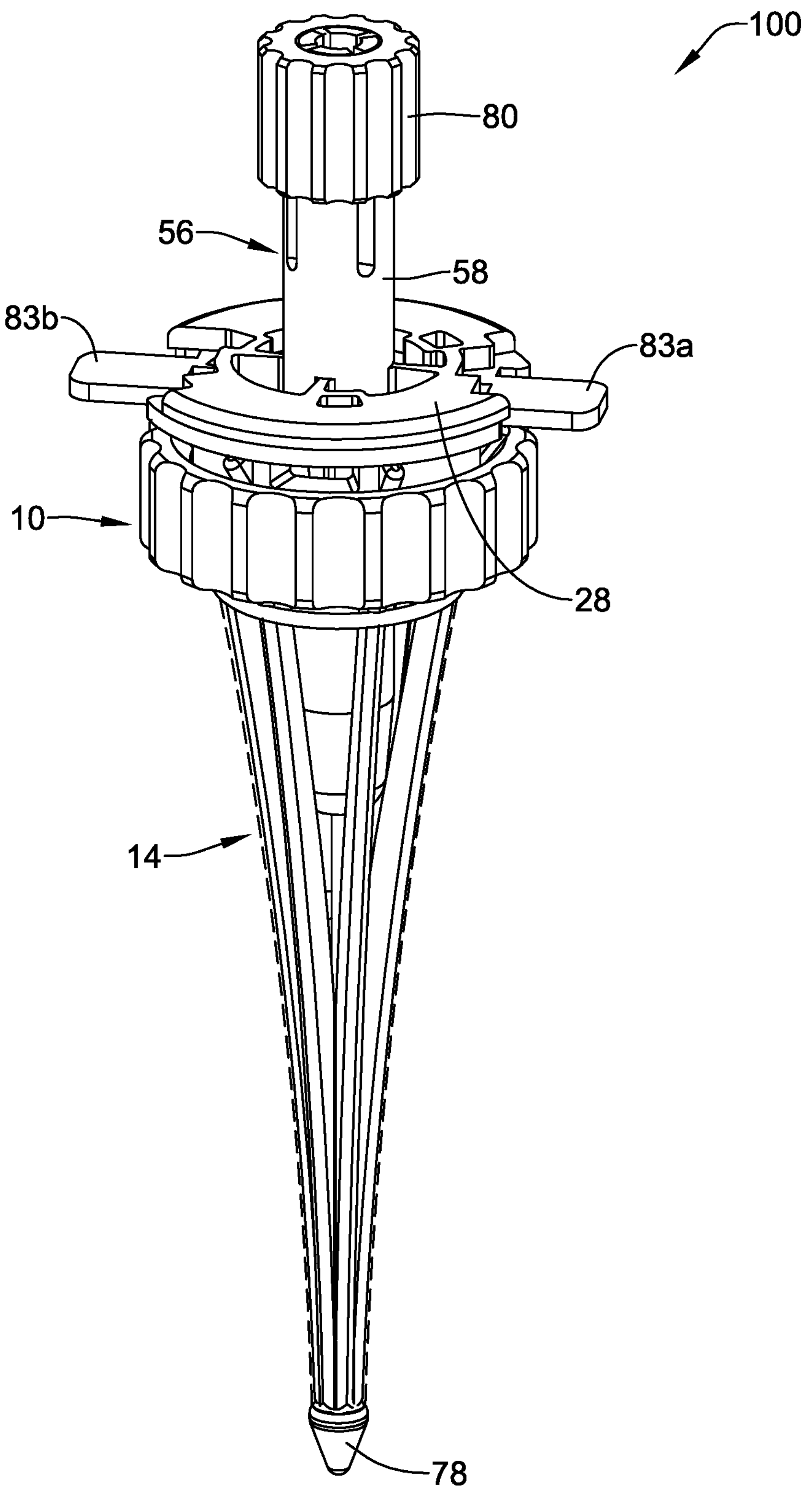
FIG. 11 is a perspective view of a system for accessing the central nervous system.

FIGS. 10-11 illustrates a system 100 that includes the expandable access port 10 along with a holder 56. The holder 56 may include a tubular body 58 and a flange 60 disposed along the tubular body 58. In some instances, a nut or grip region 80 may be disposed along the tubular body 58. The holder 56 may include a shaft 76 extending from the tubular body 58 and a nose cone 78 may be coupled to the shaft 76. The shaft 76 and the nose cone 78 may be designed so that the holder 56 can be inserted into the expandable access port 10 and, when fully inserted, the nose cone 78 may be disposed at the distal end of the expandable access port 10. In some instances, the nose cone 78 may have a generally atraumatic shape. For example, the nose cone 78 may include a tapered proximal end region and/or a tapered distal end region. This may allow the nose cone 78 to more easily be inserted into and through the expandable access port 10 and/or more easily removed from the expandable access port 10. When doing so, the expandable access port 10 may partially expand or flex while allowing the nose cone 78 to pass therethrough. Furthermore, the nose cone 78 (and/or the holder 56, in general) can be inserted into or removed from the expandable access port 10 without having to shift the expandable conduit 14 to the expanded configuration.

Figure 12:
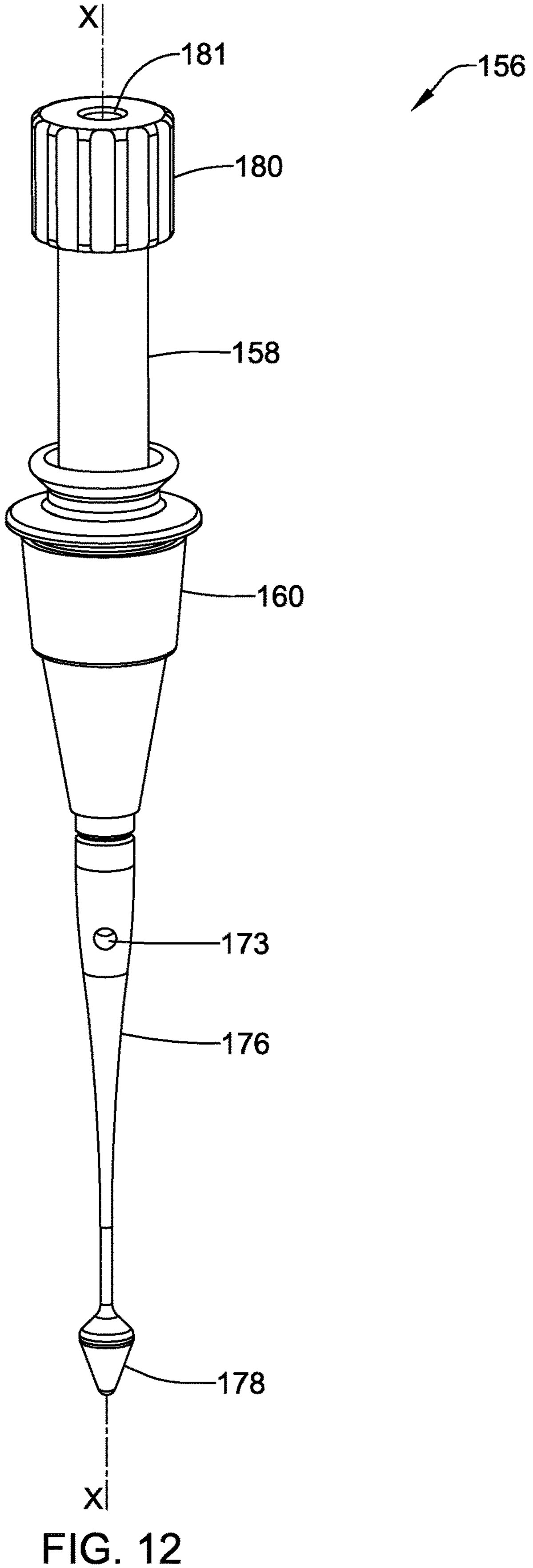
FIG. 12 is a perspective view of an example holder.
Figure 13:
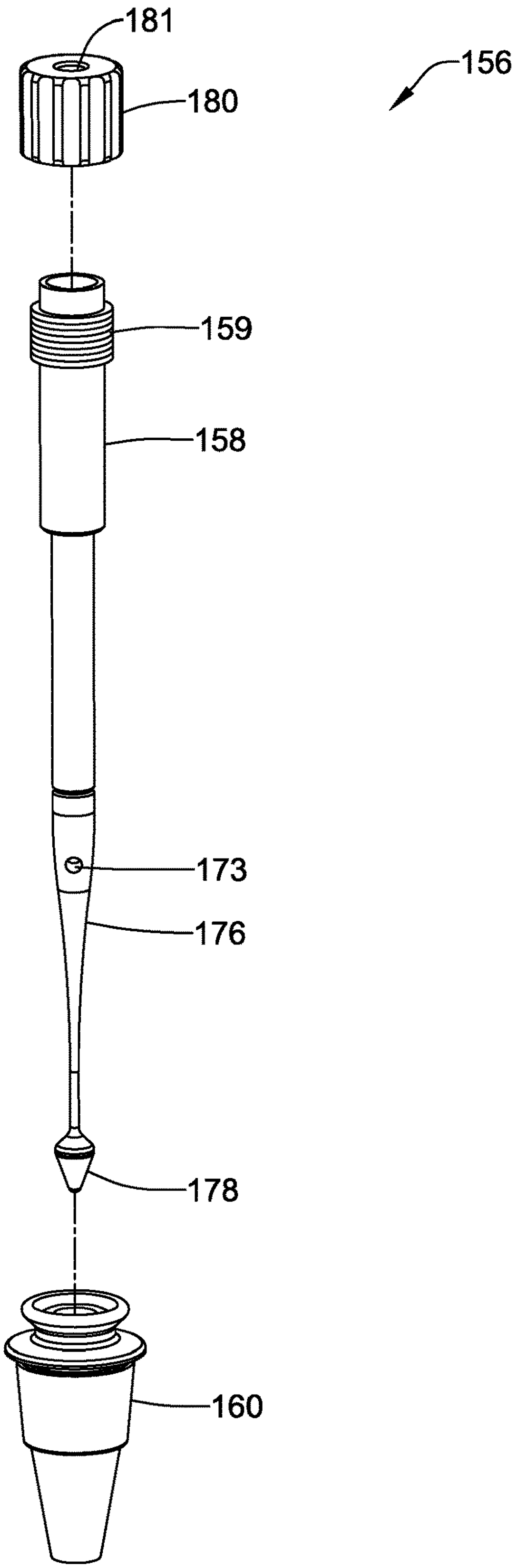
FIG. 13 is an exploded view of the holder of FIG. 12.
Figure 14:
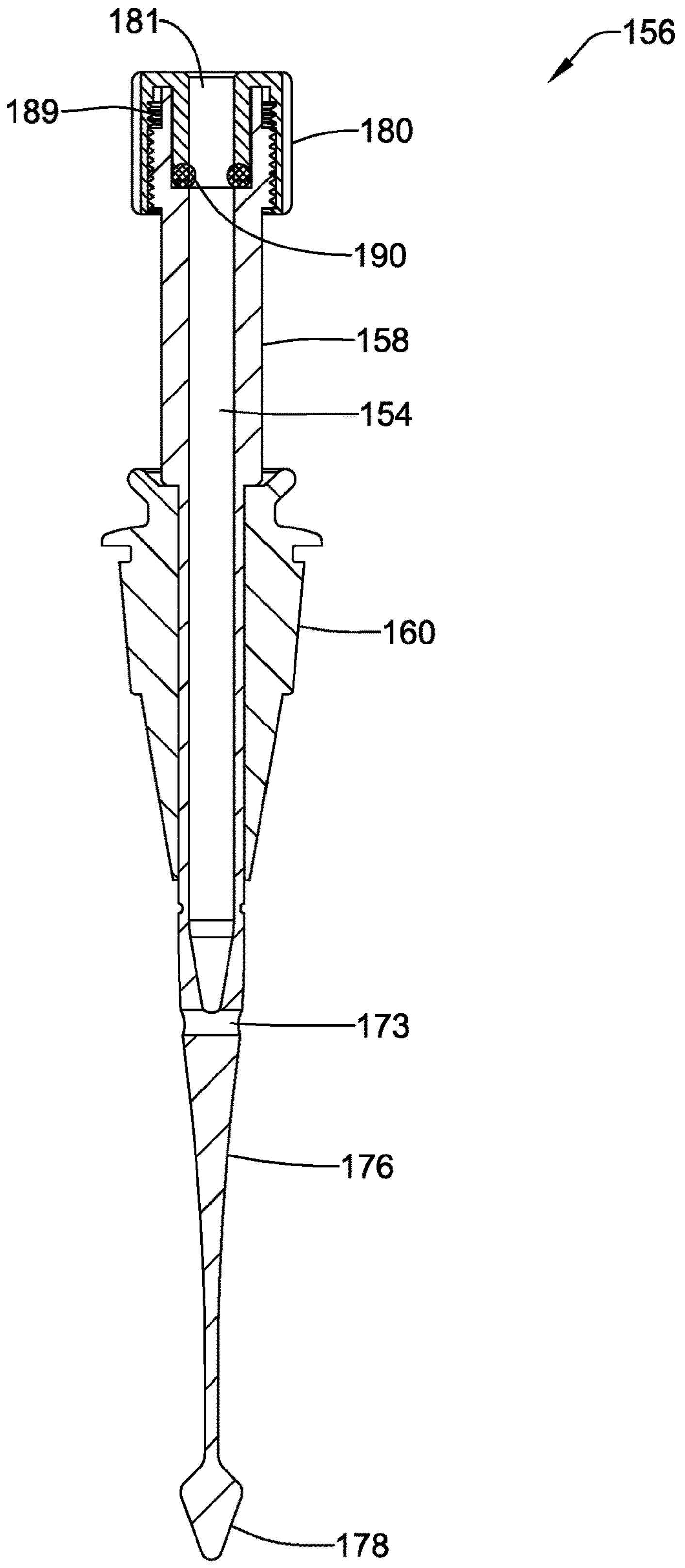
FIG. 14 is a front cross-sectional view of the holder of FIG. 12.

FIGS. 12-14 illustrate an alternate holder 156 that may be used with the expandable access port 10 described herein. As shown in FIG. 12, the holder 156 may include an obturator 158 and guide 160. The obturator 158 may include a lock 180 coupled to the proximal end. The lock 180 may have an opening 181 in its distal end face. The obturator 158 may have an opening or window 173 extending completely through the obturator 158 transverse to a longitudinal axis x-x. The window 173 may allow for a visual confirmation that a pointer tip (not shown) is fully seated within the obturator 158. The obturator 158 may have a tapered distal shaft 176 and a nose cone 178. In some examples, the obturator 158, including the distal shaft 176 and nose cone 178, may be a single monolithic element. As shown in FIG. 13, the lock 180 may be coupled to the obturator 158 via a threaded connection. The proximal end of the obturator 158 may have external threading 159 that mates with internal threading (189; see FIG. 14) on the lock 180. The guide 160 and obturator 158 may be separate elements with the obturator 158 being insertable into a lumen in the guide 160. The guide 160 may be configured to mate with the access port 10. As shown in the cross-section in FIG. 14, the opening 181 in the lock 180 is in communication with a lumen 154 extending partially through the obturator 158, from the proximal end and connecting with the window 173. In some examples, the window 173 is offset from the distal end of the nose cone 178 by about 50 mm to 55 mm, for example 52 mm. In some examples, an O-ring 190 may be positioned within the proximal end of the lumen 154 of the obturator 158, to compress and secure a pointer shaft (not shown).

The shaft 176 and the nose cone 178 may be designed so that the holder 156 can be inserted into the expandable access port 10 and, when fully inserted, the nose cone 178 may be disposed at the distal end of the expandable access port 10. In some instances, the nose cone 178 may have a generally atraumatic shape. For example, the nose cone 178 may include a tapered proximal end region and/or a tapered distal end region. In some examples, the nose cone 178 may have a diameter of 5 mm to 10 mm, for example 6 mm. This may allow the nose cone 178 to more easily be inserted into and through the expandable access port 10 and/or more easily removed from the expandable access port 10. When doing so, the expandable access port 10 may partially expand or flex while allowing the nose cone 178 to pass therethrough. Furthermore, the nose cone 178 (and/or the holder 156, in general) can be inserted into or removed from the expandable access port 10 without having to shift the expandable conduit 14 to the expanded configuration.

The materials that can be used for the various components of the expandable access port 10 may include those commonly associated with medical devices. For simplicity purposes, the following discussion makes reference to the expandable access port 10. However, this is not intended to limit the devices and methods described herein, as the discussion may be applied to other similar medical devices and/or system disclosed herein.

The expandable access port 10 may be made from a metal, metal alloy, polymer (some examples of which are disclosed below), a metal-polymer composite, ceramics, combinations thereof, and the like, or other suitable material. Some examples of suitable polymers may include polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites, and the like. In some embodiments the sheath can be blended with a liquid crystal polymer (LCP). For example, the mixture can contain up to about 6 percent LCP.

Some examples of suitable metals and metal alloys include stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R30035 such as MP35-NR and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material.

U.S. Patent Application Pub. No. US 2019/0247087 is herein incorporated by reference.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

What is claimed is:

1. An expandable access port, comprising:
- a housing;
- a plurality of tines, each tine having a proximal end region coupled to the housing, each tine configured to move between a compressed configuration and an expanded configuration;
- a thrust washer coupled to an outer surface of the housing, the thrust washer configured to engage the proximal end regions of the plurality of tines; and
- an actuation member threadedly coupled to the outer surface of the housing, the actuation member including a radially inwardly extending flange configured to engage the proximal end region of each of the plurality of tines, wherein rotation of the actuation member causes the flange to shift the plurality of tines between the compressed configuration and the expanded configuration.

2. The expandable access port of claim 1, wherein the flange is positioned adjacent an internally threaded region of the actuation member.

3. The expandable access port of claim 2, wherein the flange is positioned proximal of the internally threaded region of the actuation member.

4. The expandable access port of claim 1, the thrust washer including a plurality of cutout regions each configured to directly engage the proximal end region of one of the plurality of tines.

5. The expandable access port of claim 4, wherein portions of the thrust washer between adjacent cutout regions engage the housing to secure the thrust washer in place.

6. The expandable access port of claim 1, wherein the thrust washer is positioned proximal of the flange.

7. The expandable access port of claim 1, wherein frictional forces between the housing and the actuation member hold the tines in the expanded configuration.

8. The expandable access port of claim 1, wherein when the actuation member is in a distal position, the plurality of tines are in the compressed configuration and when the actuation member is in a proximal position, the plurality of tines are in the expanded configuration.

9. The expandable access port of claim 1, further comprising a sleeve extending along at least some of the plurality of tines.

10. The expandable access port of claim 9, wherein the sleeve includes a biocompatible elastomer.

11. The expandable access port of claim 9, wherein distal ends of the plurality of tines each include a crimp configured to receive and secure an end portion of the sleeve.

12. An expandable access port, comprising:
- a housing;
- a plurality of tines, each tine having a proximal end region coupled to the housing, the proximal end region including an angled surface extending radially outward, each tine configured to move between a compressed configuration and an expanded configuration;
- a thrust washer coupled to an outer surface of the housing, the thrust washer configured to engage the proximal end regions of the plurality of tines; and
- an actuation member rotatably coupled to the outer surface of the housing, the actuation member including an actuation surface configured to engage the angled surface of each of the plurality of tines, wherein rotation of the actuation member causes the actuation surface to shift the plurality of tines between the compressed configuration and the expanded configuration.

13. The expandable access port of claim 12, the thrust washer including a plurality of cutout regions each configured to directly engage the proximal end region of one of the plurality of tines.

14. The expandable access port of claim 13, wherein portions of the thrust washer between adjacent cutout regions engage the housing to secure the thrust washer in place.

15. The expandable access port of claim 12, wherein the thrust washer is positioned proximal of the actuation surface.

16. The expandable access port of claim 12, wherein frictional forces between the housing and the actuation member hold the tines in the expanded configuration.

17. The expandable access port of claim 12, wherein when the actuation member is in a distal position, the plurality of tines are in the compressed configuration and when the actuation member is in a proximal position, the plurality of tines are in the expanded configuration.

18. The expandable access port of claim 12, further comprising a sleeve extending along at least some of the plurality of tines.

19. The expandable access port of claim 18, wherein the sleeve includes a biocompatible elastomer.

20. An expandable access port, comprising:
- a housing having an externally threaded region;
- a plurality of tines, each tine having a proximal end region coupled to the housing, each tine configured to move between a compressed configuration and an expanded configuration;
- a thrust washer coupled to an outer surface of the housing proximal of the externally threaded region, the thrust washer configured to engage the proximal end regions of the plurality of tines; and
- an actuation member having an internally threaded region threadedly coupled to the externally threaded region of the housing, the actuation member including an actuation surface positioned proximal of the internally threaded region and configured to engage the proximal end region of each of the plurality of tines, wherein rotation of the actuation member relative to the housing causes the actuation surface to shift the plurality of tines between the compressed configuration and the expanded configuration.

* * * * *